US012616786B2

(12) United States Patent
Irrgang

(10) Patent No.: US 12,616,786 B2
(45) Date of Patent: May 5, 2026

(54) DIALYSIS MACHINE AND METHOD OF OPERATING A BALANCING CHAMBER SYSTEM OF A DIALYSIS MACHINE

(71) Applicant: Fresenius Medical Care Deutschland GmbH, Bad Homburg (DE)

(72) Inventor: Tobias Irrgang, Aubstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 778 days.

(21) Appl. No.: 17/625,121

(22) PCT Filed: Jul. 9, 2020

(86) PCT No.: PCT/EP2020/069426
§ 371 (c)(1),
(2) Date: Jan. 6, 2022

(87) PCT Pub. No.: WO2021/005173
PCT Pub. Date: Jan. 14, 2021

(65) Prior Publication Data
US 2022/0241483 A1      Aug. 4, 2022

(30) Foreign Application Priority Data

Jul. 9, 2019    (DE) ..................... 10 2019 118 548.3

(51) Int. Cl.
*A61M 1/34*          (2006.01)
(52) U.S. Cl.
CPC .................................. *A61M 1/3401* (2022.05)
(58) Field of Classification Search
CPC ....................................................... A61M 1/16
See application file for complete search history.

(56) References Cited

U.S. PATENT DOCUMENTS 4,267,040 A * 5/1981 Schal .................. A61M 1/1639
                                                           210/257.2
4,770,769 A * 9/1988 Schael ................ A61M 1/1639
                                                           210/257.2
(Continued)

FOREIGN PATENT DOCUMENTS

DE           28 38 414        3/1980
DE           19830928 C1 * 5/1999 .............. A61M 1/16
(Continued)

OTHER PUBLICATIONS

DE19830928C1 Translated description (Year: 1999).*
(Continued)

*Primary Examiner* — Benjamin L Lebron
*Assistant Examiner* — Marriah Ellington
(74) *Attorney, Agent, or Firm* — Kilyk & Bowersox, P.L.L.C.

(57)          ABSTRACT

A dialysis machine has a dialyzer having a first balancing chamber and a second balancing chamber, of which each has at least two first and second balancing chamber halves separated from one another by a movable wall. Each first balancing chamber half has a respective first inflow and a respective first outflow, with the first inflows of the first balancing chamber halves being in fluid communication with a source of fresh dialysate. The first outflow of the first balancing chamber half is in fluid communication with a dialyzer inflow, and the second inflows of the second balancing chamber halves are in fluid communication with a dialyzer outflow. The second outflows of the second balancing chamber halves are in fluid communication with one another so that consumed dialyzate is transferrable from a second balancing chamber half of one balancing chamber to a second balancing chamber half of the other balancing chamber.

14 Claims, 2 Drawing Sheets

(56) References Cited

U.S. PATENT DOCUMENTS

| | | | | |
|---|---|---|---|---|
| 4,935,125 A | * | 6/1990 | Era | A61M 1/1639 |
| | | | | 210/257.2 |
| 5,580,460 A | * | 12/1996 | Polaschegg | A61M 1/1601 |
| | | | | 210/138 |
| 10,245,370 B2 | | 4/2019 | Kelly et al. | |

FOREIGN PATENT DOCUMENTS

| | | | |
|---|---|---|---|
| JP | 2008-93193 | | 4/2008 |
| JP | 2008093193 A | * | 4/2008 |
| WO | WO 2015/118046 | | 8/2015 |

OTHER PUBLICATIONS

DE-19830928-C1 translated (Year: 1999).*
JP-2008093193-A translated (Year: 2008).*
Hamm et al. Kidney International, vol. 21(1982), pp. 416-418 (Year: 1982).*
Bernard Canaud, et al. Kidney International, 2015, 88 (5), pp. 1108-1116. 10.1038/ki.2015.139. hal-01997128 (Year: 2015).*
Imamovic et al. Int Urol Nephrol (2014) 46:1191-1200 (Year: 2014).*
Krieter et al. Nephrol Dial Transplant (2005) 20: 155-160. doi:10.1093/ndt/gfh520 (Year: 2005).*

* cited by examiner

DIALYSIS MACHINE AND METHOD OF OPERATING A BALANCING CHAMBER SYSTEM OF A DIALYSIS MACHINE

BACKGROUND OF THE INVENTION

1. Field of the Invention

The present invention relates to a dialysis machine having a dialyzer and having a first balancing chamber A and having a second balancing chamber B of which each has at least two first and second balancing chamber halves separated from one another by a movable wall, wherein each first balancing chamber half is provided with a respective first inflow and with a respective first outflow, wherein each second balancing chamber half is provided with a respective second inflow and with a respective second outflow, wherein the inflows and outflows are each provided with valves that are configured to close or to open the respective inflow or outflow, wherein the respective first inflow of the first balancing chamber halves is in fluid communication with a source of fresh dialyzate and the respective first outflow of the first balancing chamber halves is in fluid communication with a dialyzer inflow, and wherein the respective second inflow of the second balancing chamber halves is in fluid communication with a dialyzer outflow.

2. Description of Related Art

Such a dialysis machine is known from the prior art and is shown by way of example in FIG. 2.

FIG. 2 shows a dialysis machine in the state of "normal" hemodialysis without substitute conveying.

As can be seen from FIG. 2, two balancing chambers A and B are provided of which each has a first balancing chamber half 100, 102 and a second balancing chamber half 200, 202. The balancing chamber halves are each separated from one another by a movable wall W.

It furthermore results from FIG. 2 that each balancing chamber half 100, 200, 102, 202 has a respective first inflow Z1 and Z3 for fresh dialyzate that is supplied via the line 10 and a respective second inflow Z2 and Z4 for consumed dialyzate that is supplied from the dialyzer D via the line 20. The inflows Z1 and Z2 of the first balancing chamber A are closable by means of the valves 1.1 and 1.3; the outflows A1 and A2 of the first balancing chamber A are closable by means of the valves 1.2 and 1.4. The inflows Z3 and Z4 of the second balancing chamber B are closable by means of the valves 1.5 and 1.7 and the outflows A3 and A4 of the second balancing chamber B are closable by means of the valves 1.6 and 1.8.

The lines in which consumed dialyzate is conveyed are shown dashed in the Figures. Lines in which fresh dialyzate is conveyed are shown by solid lines.

The line 30 is in fluid communication with the outflows A1 and A3 and serves the conveying of fresh dialyzate to the dialyzer D or to its inflow DZ. The latter is divided by the membrane M into two or more than two chambers of which one is flowed through by dialyzate and the other is flowed through by blood B. The consumed dialyzate D including the ultrafiltrate moves on the outflow side DA of the dialyzer D into the secondary air separator S that has a valve V for leading off air.

A portion of the consumed dialyzate is conveyed by means of the ultrafiltration pump UF by means of the line 60 from the secondary air separator S into the drain 1. The remaining portion of the consumed dialyzate moves in a cycled manner via the inflows Z2 and Z4 to the two second balancing chamber halves 200, 202 of the balancing chambers A and B.

The line 40 is in fluid communication with the outflows A2 and A4 of the second balancing chamber halves 200, 202 and serves the conveying of consumed dialyzate to the drain 1.

The balanced conveying of the dialyzate is configured as follows in accordance with FIG. 2:

First, fresh dialyzate is conveyed via the line 10 into the first balancing chamber half 100 of the first balancing chamber A. The valve 1.1 is open and the valve 1.2 is closed for this purpose. Consumed dialyzate is simultaneously removed from the second balancing chamber half 200 of the first balancing chamber A via the line 40 into the drain 1 by the wall W moving to the right here. The valve 1.3 is closed and the valve 1.4 is open here. Exactly one balancing chamber volume is thus conveyed, for example 30 ml.

The second balancing chamber B works in a counter-cycle, i.e. valve 1.5 is closed, valve 1.6 is open, valve 1.7 is open, and valve 1.8 is closed. Overall, consumed dialyzate is conveyed from the first balancing chamber A through the first balancing chamber A in this cycle and fresh dialyzate is conveyed out of the second balancing chamber B.

Subsequently, a new cycle of the balancing chamber system takes place in which fresh dialyzate is conveyed from the first balancing chamber half 100 of the first balancing chamber A and consumed dialyzate is conveyed from the second balancing chamber half 202 of the second balancing chamber B.

The above-described procedure is repeated in a constant sequence.

It is always the same amount of fresh dialyzate and consumed dialyzate that is conveyed and exactly balanced.

Due to the removal of fluid from the patient, ultrafiltrate is additionally produced on the side of the consumed dialyzate and is conveyed through the pump UF that is located in the line 60.

Approximately 2 l of ultrafiltrate per patient and a treatment time of approximately 4 h result in a treatment.

The ultrafiltrate amount is controlled via the ultrafiltrate pump UF that removes the ultrafiltrate from the blood of the patient.

The arrangement in accordance with FIG. 2 known from the prior art provides an exact monitoring of the dialysis fluid amounts (fresh and consumed) and of the ultrafiltrate amount. The control of the ultrafiltrate amount is important because a minimum amount has to be ensured to avoid a hyperhydration of the patient and, on the other hand, too fast a fluid removal can result in circulatory failure.

Provision can be made in accordance with the prior art that an additional dialyzate amount or liquid amount is conveyed to the patient via a separate pump (substitute pump), not shown. This is necessary when a larger amount of ultrafiltrate is removed from the blood than was pre-scribed for the patient. The substitute can then (as a rule) be supplied downstream of the dialyzer. An addition upstream or upstream and downstream of the dialyzer is generally also possible. Substitute amounts between 20 and 40 l per treatment cycle are typical.

This method is called HDF (hemodiafiltration). The HDF mode has the advantage that an increased convective portion can be conveyed via the dialyzer membrane and the medium molecular weight uremic toxins can thus in particular be especially effectively removed that can only be conveyed diffusively over the membrane to a small degree.

In known devices, a further filter for the substitute is required in addition to the substitute pump, said further filter ensuring a germ free filtration of the substitute. This is required because the substitute is directly infused into the patient's blood.

Such an arrangement is thus complicated and expensive.

SUMMARY OF THE INVENTION

It is thus the underlying object of the present invention to further develop a dialysis machine of the initially named kind such that it has a design that is as simple as possible.

This object is achieved by a dialysis machine having a dialyzer (D) and having a first balancing chamber (A) and having a second balancing chamber (B) of which each has at least two first (100, 102) and second balancing chamber halves (200, 202) separated from one another by a movable wall (W), wherein each first balancing chamber half (100, 102) is provided with a respective first inflow (Z1, Z3) and with a respective first outflow (A1, A3), wherein each second balancing chamber half (200, 202) is provided with a respective second inflow (Z2, Z4) and with a respective second outflow (A2, A4), wherein the inflows and outflows (A1-A4, Z1-Z4) are each provided with valves (1.1-1.4; 2.1-2.4) that are configured to close or to open the respective inflow (Z1-Z4) or outflow (A1-A4), wherein the first inflows (Z1; Z3) of the first balancing chamber halves (100) are in fluid communication with a source of fresh dialyzate and the first outflow (A1) of the first balancing chamber half (100) is in fluid communication with a dialyzer inflow, and wherein the second inflows (Z2; Z4) of the second balancing chamber halves (200; 202) are in fluid communication with a dialyzer outflow, characterized in that the second outflows (A2; A4) of the second balancing chamber halves (200, 202) are in fluid communication with one another so that consumed dialyzate is transferrable from a second balancing chamber half (200) of a balancing chamber (A) to a second balancing chamber half (202) of the other balancing chamber (B). Provision is accordingly made that the second outflows of the second balancing chamber halves are in fluid communication with one another so that consumed dialyzate can be transferred from a second balancing chamber half of a balancing chamber to a second balancing chamber half of the other balancing chamber. Provision is thus made in accordance with the invention that the outflows of the second balancing chamber halves are preferably directly connected to one another and a volume (oscillating volume) is conveyed from a second balancing chamber half of a balancing chamber to a second balancing chamber half of the other balancing chamber.

Consumed dialyzate is thus not conveyed into the outflow in the balancing chamber cycle, a specific amount of the consumed dialyzate rather serves as an oscillating volume that is conducted from one balancing chamber to the other balancing chamber. This procedure can take place once or multiple times, i.e. the volume can also oscillate to and fro.

Since no consumed dialyzate is removed from the system in this case, as is, however, the case in accordance with the prior art, but rather fresh dialyzate continues to be added, the fluid amount in the system is increased. This fluid amount is conveyed over the membrane M of the dialyzer D into the patient and thus reaches the blood B.

The fluid amount (e.g. 1 stroke, 30 ml) serves as a substitute for the patient. At the same time, the membrane M of the dialyzer D acts as a sterile filter for the substitute so that both a substitute pump and a sterile filter are obsolete. Apart from this, no separate tubing kit is required for the substituate.

Provision is preferably made that the second outflows of the second balancing chamber halves are in fluid communication with a drain line which leads to an outlet, in which a drain valve is arranged, and by means of which the drain line can be opened and closed. Provision is preferably made during the above-described oscillating movement that this drain valve is closed.

It is conceivable that a control unit is provided that is configured to control the valves such that with an open first inflow and a closed first outflow of the first balancing chamber half of the first balancing chamber, this first balancing chamber half is filled with fresh dialyzate, such that in this process with a closed second inflow and an open second outflow, the second balancing chamber half of this first balancing chamber is emptied, with the second outflow of the second balancing chamber half being opened so that the consumed dialyzate is conveyed from the second balancing chamber half of the first balancing chamber into the second balancing chamber half of the second balancing chamber, with the first outflow of the second balancing chamber half of the second balancing chamber being opened and the first inflow of the second balancing chamber half of the second balancing chamber being closed so that fresh dialyzate is conveyed from the second balancing chamber half to the dialyzer.

The process naturally also applies in reverse order, i.e. for a conveying of the oscillating volume from the second balancing chamber to the first balancing chamber.

Provision is preferably made that the machine does not have any substitute pump for conveying a substitute solution into the blood of the patient.

As stated, a control can be provided that is configured to close the drain valve when consumed dialyzate is transferred from a second balancing chamber half of a balancing chamber to a second balancing chamber half of the other balancing chamber.

A control can furthermore be provided that is configured to control the valves such that consumed dialyzate is transferred from a second balancing chamber half of a balancing chamber to a second balancing chamber half of the other balancing chamber and that the second outflows of the second balancing chamber halves are moved into fluid communication with an outlet for consumed dialyzate after this transfer or after a plurality of such transfers.

After one or more conveying processes to and fro of the oscillating volume, provision is made in this case that the consumed dialyzate is supplied to the drain.

It is conceivable that a control is provided that is configured to carry out the transfer of consumed dialyzate, i.e. of the oscillating volume, at each nth cycle of the operation of the balancing chamber system. In this case, the oscillating movement takes place e.g. at each 10th cycle of the balancing chamber system.

It is furthermore conceivable that a control is provided that is configured to carry out the transfer of consumed dialyzate from the second balancing chamber half of a balancing chamber to the second balancing chamber half of the other balancing chamber distributed evenly in time or unevenly in time over the treatment duration. The points in time at which the transfer of the oscillating volume, i.e. the oscillating movement, takes place can depend, for example, on a prescription of a physician.

The dialyzer is preferably a high-flux dialyzer or a medium cut-off dialyzer. Filters are called high-flux dialyzers that have an ultrafiltration rate of 20-70 mL/m2*mmHg*h in human blood. In these dialyzers, the substitute supply in accordance with the invention is particularly easy to achieve due to the high water permeability in the full blood. In this respect, substitute amounts of 5 to 25 l per 4 hour treatment are preferably set, particularly preferably 15 to 25 l per 4 hour treatment.

The dialysis machine in accordance with the invention is particularly efficient in medium cut-off dialyzers or protein leaking dialyzers. Such dialyzers have an even higher ultrafiltration rate in full blood than high-flux dialyzers; however, the increased albumin loss that can amount to up to 8 g in a treatment of 4 hours has proved to be disadvantageous. In medium cut-off dialyzers, a substitute supply takes place by uncontrolled back filtration. The substitute amount can be exactly controlled by a dialysis machine in accordance with the invention. Higher substitute amounts are in particular also possible than with a dialysis machine in accordance with the prior art that is operated with a medium cut-off dialyzer. The optimum substitute amount can thus also be provided while taking account of the permitted albumin loss with different hematocrit values of the patient's blood. Substitute amounts of 5-20 l can be set in accordance with the invention with a 4 hour HD treatment. Substitute amounts of 8 to 15 l per 4 hour treatment are preferred.

The present invention further relates to a method of operating a balancing chamber system having a first balancing chamber and having a second balancing chamber of which each has at least two first and second balancing chamber halves separated from one another by a movable wall, wherein each first balancing chamber half is provided with a respective first inflow and with a respective first outflow, wherein each second balancing chamber half is provided with a respective second inflow and with a respective second outflow, wherein the inflows and outflows are each provided with valves that are configured to close or to open the respective inflow or outflow, wherein the first inflow of the first balancing chamber halves is in fluid communication with a source of fresh dialyzate and the first outflow of the first balancing chamber halves is in fluid communication with a dialyzer inflow, and wherein the second inflow of the second balancing chamber halves is in fluid communication with a respective dialyzer outflow, with dialyzate consumed in a first operating mode being transferred from the second balancing chamber half of the first balancing chamber to the second balancing chamber half of the second balancing chamber, while the first balancing chamber half of the first balancing chamber is filled with fresh dialyzate and consumed dialyzate is emptied from the second balancing chamber half of the second balancing chamber.

In the first operating mode, consumed dialyzate can also be transferred from the second balancing chamber half of the second balancing chamber to the second balancing chamber half of the first balancing chamber, while the first balancing chamber half of the second balancing chamber is filled with fresh dialyzate and consumed dialyzate is emptied from the second balancing chamber half of the first balancing chamber.

The transfer of the oscillating volume can thus take place from the first to the second balancing chambers and also conversely from the second to the first balancing chambers.

The transfer of the oscillating volume from one balancing chamber to the other can take place once or multiple times.

The transfer can take place a plurality of times directly after one another or with interposed cycles of the balancing chamber without transfer.

It is also conceivable that dialyzate consumed in a second operating mode is conveyed from each of the second balancing chamber halves into the outlet. In this case, no oscillating volume is present and the dialysis machine is operated as is known from the prior art.

As stated, it is of advantage if no substitute pump is used for the supply of substitute to the patient. Such a substitute pump can be dispensed with since the excess amount of fresh dialyzate is supplied to the patient over the membrane of the dialyzer.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

BRIEF DESCRIPTION OF THE DRAWINGS

Further details and advantages of the invention will be explained in more detail with reference to an embodiment shown in the drawing.

There are shown.

Elements that are the same or have the same function are marked in FIG. 1 by the same reference numerals as in FIG. 2 so that reference is made accordingly.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The operation of the dialysis machine in accordance with the invention is configured as follows.

First, the first balancing chamber half 100 of the first balancing chamber A is in turn filled with fresh dialyzate; V1.1 is open and V1.2 is closed; V1.3 is closed and V1.4 is open. The first balancing chamber half 100 is thus filled with fresh dialyzate and consumed dialyzate is removed from the second balancing chamber half 200 of the first balancing chamber A.

A reverse cycle is in turn set in the second balancing chamber B.

Fresh dialyzate is removed from the balancing chamber half 102, with the valve V2.1 being closed and V2.2 being open. Valve V2.4 is now opened and V2.3 remains closed. A switchover to the opposite cycle again takes place on the conclusion of the process.

This switching has the result that consumed dialyzate is moved between the two balancing chambers or is moved to and fro.

Figure 1:
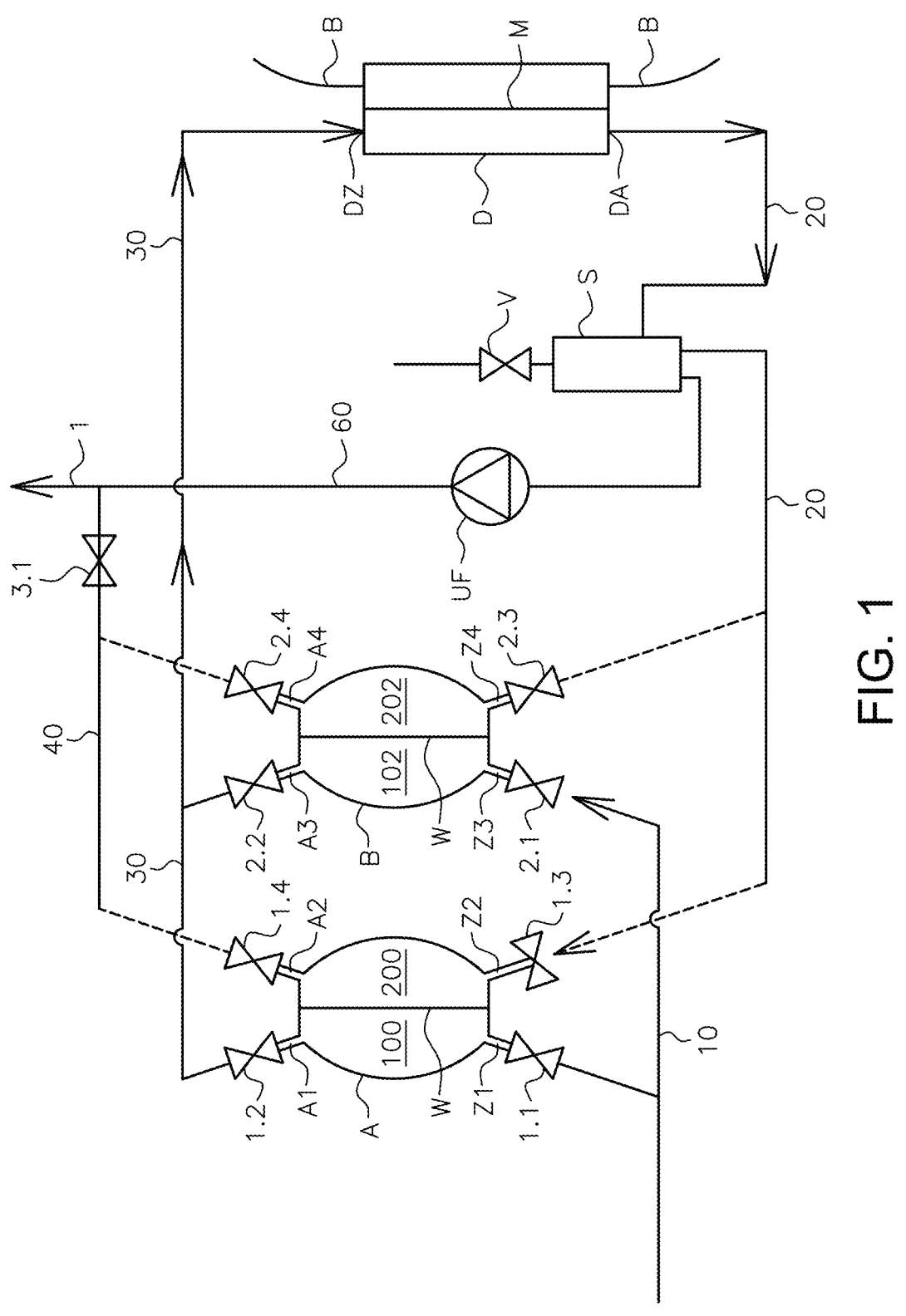
FIG. 1: a schematic view of the dialyzate circuit of a dialysis machine in accordance with the invention.
Figure 2:
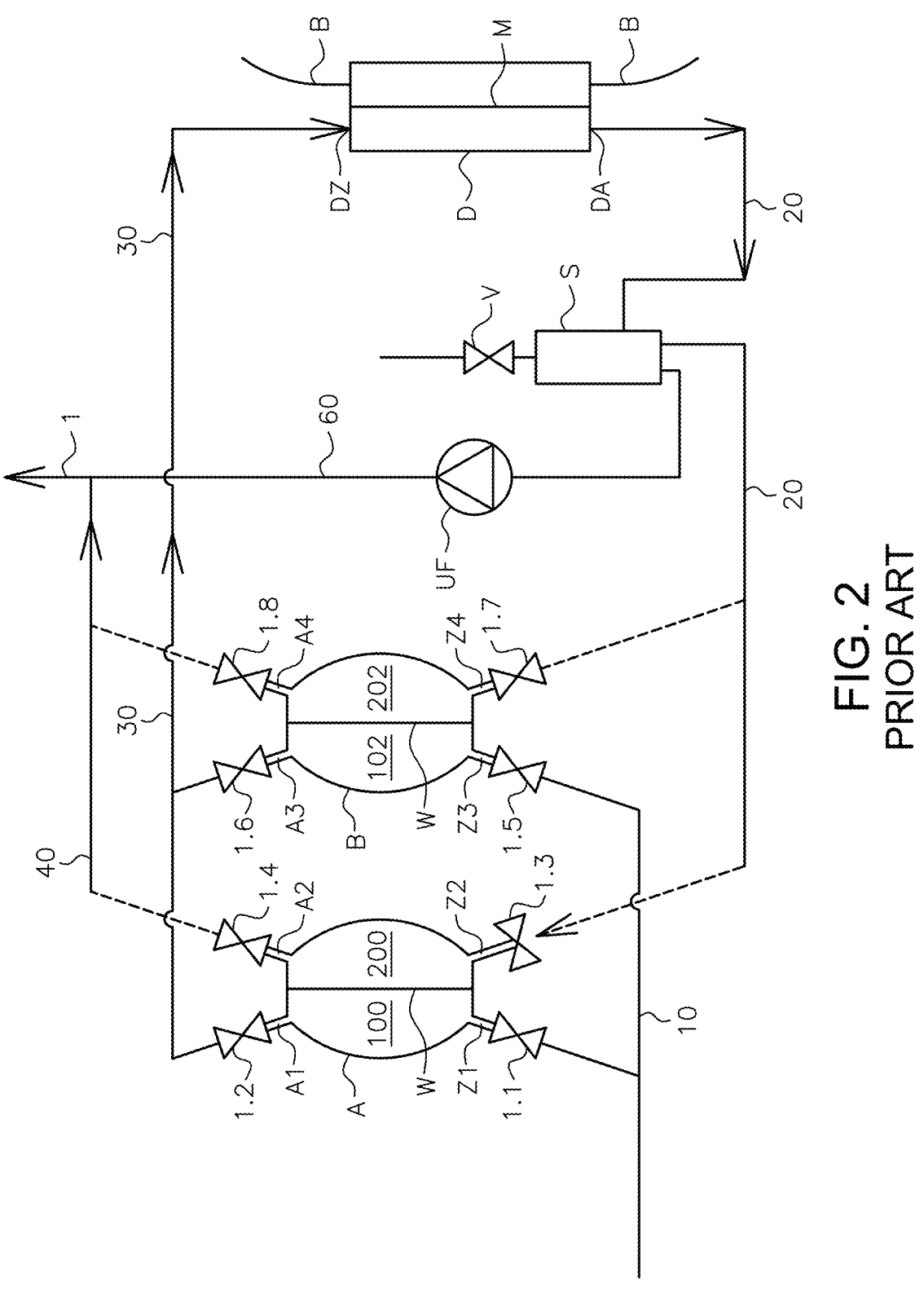
FIG. 2: a schematic view of the dialysis circuit of a dialysis machine in accordance with the prior art.

Consumed dialyzate is thus no longer removed from the system in this operating mode, as is the case in the situation of FIG. 2. However, since further fresh dialyzate is conveyed into the system, the fluid amount increases. This fluid amount is conveyed over the membrane of the dialyzer into the patient so that this fluid amount (at least one stroke, for example 30 ml) acts as a substitute for the patient.

At the same time, the dialyzer membrane acts as a sterile filter for the substitute. An internal HDF mode is thus provided so that a sterile filter separately provided for this purpose is dispensed with.

There is the advantage that no separate substitute pump, no separate tubing set, and no separate sterile filter have to be provided.

Provision can be made during this oscillating movement of the consumed dialyzate from one second balancing chamber half to the other and/or vice versa that a valve 3.1 is closed downstream of the balancing chambers in the line 40.

Provision can (preferably) be made that only one filling amount of a balancing chamber is used to provide a substitute (that is, 30 ml, for example).

Provision can also be made that a "double stroke" is carried out, i.e. an amount of consumed dialyzate is therefore pushed "to" once and "fro "once".

Provision can be made that, for example, every 10th cycle is used to produce substitute.

The apparatus can comprise an evaluation and control unit that evenly distributes the medically prescribed substitute amount over the treatment duration.

The apparatus can comprise an evaluation and control unit that unevenly distributes the medically prescribed substituate amount over the treatment duration. This means that, for example, the substitute amount is higher or lower at the start of the treatment than at the end of the treatment.

The apparatus has a particularly good effect when dialyzers are used that are called high-flux dialyzers. Filters are called high-flux dialyzers that have an ultrafiltration rate of 20-70 mL/m2*mmHg*h in human blood.

The apparatus in accordance with the invention is in particular effective in conjunction with a so-called medium cut-off dialyzer. Such a dialyzer is described, for example, in WO 2015/118046 A to which reference is made to this extent. Such dialyzers have an uncontrolled back rinsing of dialyzate into the blood circuit, which is produced by the internal pressure relationships in the dialyzer. These dialyzers may not be operated in HDF mode since the loss of albumin would otherwise become significantly too high.

With the aid of the apparatus in accordance with the invention, operation can now be made in a "controlled substitute mode" with a "normal" machine. The substitute amount can in particular be limited by a skillful program selection to volumes between 2 and 15 l/treatment, preferably to volumes between 5 and 12 l/treatment, further preferably to volumes between 5 and 10 l/treatment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine comprising a dialyzer and a balancing chamber system, the dialyzer comprising a dialyzer inflow and a dialyzer outflow, the balancing chamber system comprising a first balancing chamber, a second balancing chamber, and a control unit, wherein the first balancing chamber has a first balancing chamber first half and a first balancing chamber second half that are separated from one another by a first movable wall, the first balancing chamber first half being provided with a first inflow and with a first outflow, the first balancing chamber second half being provided with a second inflow and with a second outflow, the second balancing chamber has a second balancing chamber first half and a second balancing chamber second half that are separated from one another by a second movable wall, the second balancing chamber first half being provided with a third inflow and with a third outflow, the second balancing chamber second half being provided with a fourth inflow and with a fourth outflow, each of the first, second, third, and fourth inflows and the first, second, third, and fourth outflows is provided with a respective valve that is configured to close or to open the respective inflow or outflow, the first and third inflows are in fluid communication with a source of fresh dialysate, the first outflow is in fluid communication with the dialyzer inflow, the second inflow and the fourth inflow are in fluid communication with the dialyzer outflow, the second outflow and the fourth outflow are in fluid communication with one another so that consumed dialyzate is transferrable from the first balancing chamber second half to the second balancing chamber second half or from the second balancing chamber second half to the first balancing chamber second half, and the control unit is configured to control the valves such that Configuration I is enabled, Configuration II is enabled, or both Configuration I and Configuration II are enabled, wherein, according to Configuration I: with the first inflow being open and the first outflow being closed, the first balancing chamber first half is filled with fresh dialysate with the second inflow being closed, the second outflow being open, and the fourth outflow being open, the first balancing chamber second half is emptied and consumed dialyzate is conveyed from the first balancing chamber second half of the first balancing chamber into the second balancing chamber second half of the second balancing chamber, and with the fourth outflow being open, the third outflow being open, and the third inflow being closed, fresh dialyzate is conveyed from the second balancing chamber first half to the dialyzer inflow;

and according to Configuration II: with the third inflow being open and the third outflow being closed, the second balancing chamber first half is filled with fresh dialysate with the fourth inflow being closed, the fourth outflow being open, and the second outflow being open, the second balancing chamber second half is emptied and consumed dialyzate is conveyed from the second balancing chamber second half into the first balancing chamber second half and with the second outflow being open, the first outflow being open, and the first inflow being closed, fresh dialyzate is conveyed from the first balancing chamber first half to the dialyzer inflow; and wherein the control unit is configured to control the valves such that a volume of fresh dialyzate that is conveyed to the dialyzer inflow is restricted to volumes a volume of between 2 and 15 l/treatment liters per hemodiafiltration treatment.

2. The dialysis machine in accordance with claim 1, wherein the second outflow and the fourth outflow are in fluid communication with a drain line that leads to an outlet in which a drain valve is arranged and via which the drain line is openable and closeable.

3. The dialysis machine in accordance with claim 1, wherein the dialysis machine is free of a substitute pump for conveying a substitution solution.

4. The dialysis machine in accordance with claim 2, further comprising a drain control unit that is configured to close the drain valve when consumed dialysate is transferred from the first balancing chamber second half to the second balancing chamber second half or from the second balancing chamber second half to the first balancing chamber second half.

5. The dialysis machine in accordance with claim 1, wherein the control unit is further configured to control the valves of the first, second, third, and fourth inflows and of the first, second, third, and fourth outflows such that: consumed dialyzate is transferred from the first balancing chamber second half to the second balancing chamber second half or from the second balancing chamber second half to the first balancing chamber second half and such that, after the transfer, the second outflow and the fourth outflow are moved into fluid communication with a drain line.

6. The dialysis machine in accordance with claim 5, a wherein the balancing chamber system is configured to operate cyclically for cycles of operation, and the control unit is further configured to carry out a transfer of consumed dialyzate from the first balancing chamber second half to the second balancing chamber second half, or from the second balancing chamber second half to the first balancing chamber second half, at each nth cycle of operation of the balancing chamber system.

7. The dialysis machine in accordance with claim 1, wherein the control unit is further configured to carry out a transfer of consumed dialyzate from the first balancing chamber second half to the second balancing chamber second half, or from the second balancing chamber second half to the first balancing chamber second half, evenly in time over a treatment duration.

8. The dialysis machine in accordance with claim 1, wherein the dialyzer is a high-flux dialyzer.

9. The dialysis machine in accordance with claim 1, wherein the control unit is configured to control the valves such that a volume of fresh dialyzate that is so conveyed to the dialyzer is restricted to a volume of between 5 and 12 liters per four-hour hemodiafiltration treatment.

10. The dialysis machine in accordance with claim 9, wherein the control unit is configured to control the valves such that a volume of fresh dialyzate that is conveyed to the dialyzer inflow is restricted to a volume of between 5 and 10 liters per four-hour hemodiafiltration treatment.

11. The dialysis machine in accordance with claim 1, wherein the control unit is configured to carry out a transfer of consumed dialyzate from the first balancing chamber second half to the second balancing chamber second half, or from the second balancing chamber second half to the first balancing chamber second half, unevenly in time over the treatment duration.

12. The dialysis machine in accordance with claim 1, wherein the dialyzer is a medium cut-off dialyzer.

13. The dialysis machine in accordance with claim 1, wherein the control unit is configured to control the valves such that Configuration I is enabled.

14. The dialysis machine in accordance with claim 1, wherein the control unit is configured to control the valves such that Configuration II is enabled.

* * * * *